(12) United States Patent
Poll

(10) Patent No.: US 7,771,435 B2
(45) Date of Patent: *Aug. 10, 2010

(54) FRAGMENTATION AND EXTRACTION BASKET

(75) Inventor: Wayne L. Poll, New Albany, OH (US)

(73) Assignee: Minimally Invasive Devices, LLC, Columbus, OH (US)

( * ) Notice: Subject to any disclaimer, the term of this patent is extended or adjusted under 35 U.S.C. 154(b) by 212 days.

This patent is subject to a terminal disclaimer.

(21) Appl. No.: 12/108,765

(22) Filed: Apr. 24, 2008

(65) Prior Publication Data

US 2009/0018550 A1    Jan. 15, 2009

Related U.S. Application Data

(63) Continuation of application No. 10/726,412, filed on Dec. 3, 2003, now Pat. No. 7,125,652.

(60) Provisional application No. 60/503,404, filed on Sep. 16, 2003.

(51) Int. Cl.
*A61M 17/221* (2006.01)

(52) U.S. Cl. .................................. 606/128

(58) Field of Classification Search ............... 606/108, 606/110, 113, 114, 125, 127, 128, 159, 200; 604/104–107
See application file for complete search history.

(56) References Cited

U.S. PATENT DOCUMENTS

| 5,176,688 | A * | 1/1993 | Narayan et al. | 606/128 |
| 5,197,968 | A * | 3/1993 | Clement | 606/115 |
| 5,456,667 | A * | 10/1995 | Ham et al. | 604/107 |
| 6,264,664 | B1 * | 7/2001 | Avellanet | 606/128 |
| 6,432,111 | B1 * | 8/2002 | Ternstrom | 606/114 |
| 6,500,182 | B2 * | 12/2002 | Foster | 606/127 |

* cited by examiner

*Primary Examiner*—Anhtuan T Nguyen
*Assistant Examiner*—Elizabeth Houston
(74) *Attorney, Agent, or Firm*—Porter, Wright, Morris & Arthur, LLP

(57) ABSTRACT

A surgical instrument for fragmenting and extracting stones includes an outer sheath having a proximal end and a distal end and an inner core longitudinally extending through the core and longitudinally movable relative to the core. The outer sheath has a basket sized for entrapping the stones and located near the distal end of the outer sheath. The distal end of the inner core is longitudinally moveable from a retracted position within the basket to an extended position past the distal end of the outer sheath. The distal end of the inner core is also adapted to engage and fragment the stones. Longitudinal movement of the inner core relative to the outer sheath transforms the basket from an expanded condition to a collapsed condition to entrap stones within the basket and provide a small profile for insertion and withdrawal.

17 Claims, 5 Drawing Sheets

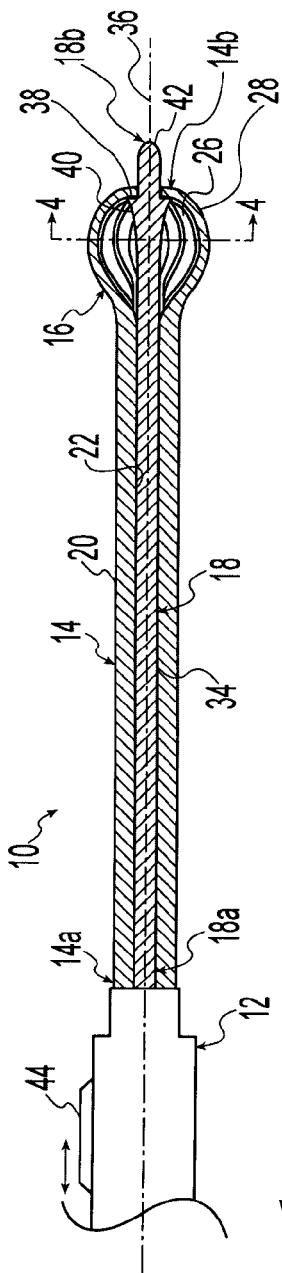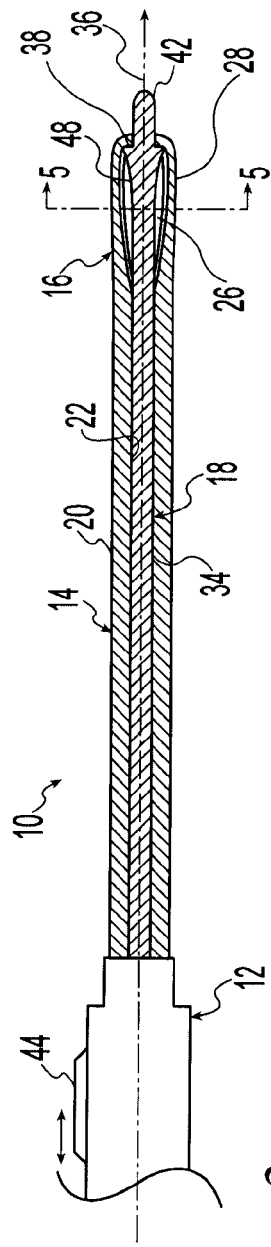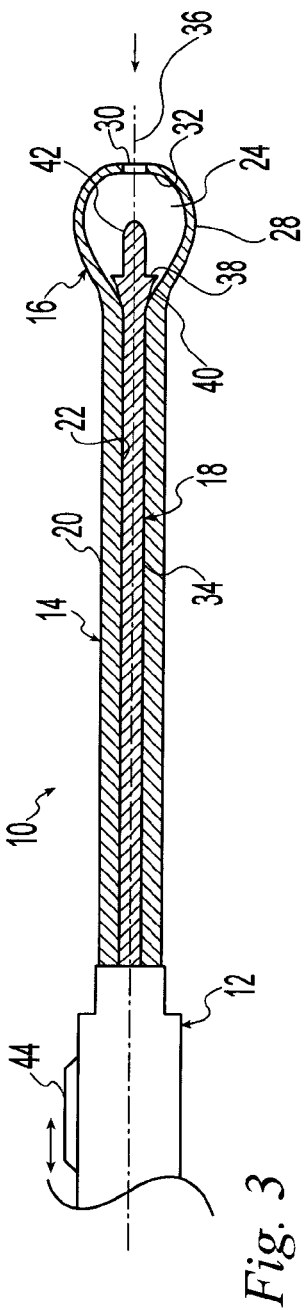

US 7,771,435 B2

FRAGMENTATION AND EXTRACTION BASKET

CROSS-REFERENCE TO RELATED APPLICATIONS

This application is a continuation application of U.S. patent application Ser. No. 10/726,412 filed on Dec. 3, 2003, now U.S. Pat. No. 7,125,652 which claims the priority benefit of provisional patent application No. 60/503,404 filed on Sep. 16, 2003, the disclosures of which are expressly incorporated herein in their entireties by reference.

STATEMENT REGARDING FEDERALLY SPONSORED RESEARCH

Not Applicable

REFERENCE TO MICROFICHE APPENDIX

Not Applicable

FIELD OF THE INVENTION

The present invention generally relates to a surgical instrument and, more particularly, to a basket type device or instrument for fragmenting and/or extracting stones or the like from various locations within a patient's body.

BACKGROUND OF THE INVENTION

Many procedures have been used for extracting stones and stone fragments such as ureteral stones, calaceal stones and other calculus and the like from various biological systems such as renal and biliary systems. For example, ureteroscopy is the passage of a narrow caliber urinary endoscope within the ureteral lumen and is most commonly performed for the treatment and removal of painful ureteral stones that will not pass spontaneously. Ureteroscopy allows stone visualization and provides access for the delivery, guidance, and actuation of stone removal and/or fragmentation devices.

Typically, stone removal is accomplished with a retrieval basket. Existing stone retrieval baskets are constructed with inner and outer components. The inner component is typically a multi-filament wire generally composed of three to four strands that naturally separate and expand to form an oval shaped basket near the end and then rejoin at their terminus to a tapered tip. The outer component is a narrow cylindrical tube generally composed of plastic that encases the inner wire core and basket. When the wire inner component is pulled through the outer member, the flexible wires collapse so as to completely withdraw into the outer casing and collapse the basket. Typically a stone retrieval basket is passed beyond the stone either without or after fragmentation. The inner core is then advanced within and past the end of the outer sheath by manipulation of a handle on the proximal (surgeon's) end of the device. The inner core filaments then expand to form the basket and the surgeon manipulates the stone into the basket. Once the stone is entrapped in the basket, the inner core is withdrawn partially into the outer sheath so as to narrow the basket and securely capture the stone. Since the inner core cannot be completely withdrawn due to entrapped stone, the outer diameter of the basket is now larger than the fully collapsed device. The degree to which the basket is narrowed is visually controlled by the surgeon so as to insure the stone is firmly trapped.

Small stones may be simply grasped with a basket passed through the working channel of the ureteroscope. However, larger stones require fragmentation into smaller particles before they can be safely removed without injury to the ureter. In some cases, the stone may be completely fragmented into pieces so small that they will naturally pass out of the patient on their own without extraction. Occasionally, stones felt to be suitable for simple extraction will become immovable within narrowed segments of the ureteral lumen after basket entrapment. It is then difficult to disengage the stone from the basket for initial or additional fragmentation, and fragmentation within the basket is complicated.

Stone fragmentation is generally carried out via ultrasonic, ballistic, or laser methods. A fragmentation device is passed through the working channel of the ureteroscope and fragmentation is then performed. Stones are not held firmly in place during fragmentation making completion of fragmentation difficult to judge, and allowing some pieces that are still too large to pass naturally, to migrate proximally up the ureter where they may be difficult to re-engage or retrieve. Generally, once fragmentation is complete, the fragmentation device is removed and the basket is passed to entrap the remaining pieces. As such, two separate devices are necessary to complete fragmentation and removal.

Fragmentation without entrapment permits stone migration and loss. Fragmentation would be far more effective if the stone were held firmly in place so it could not recoil away from the fragmenting tip. Stone entrapment either without or after some fragmentation can be problematic in that even small stones, or those initially deemed to be adequately broken up, may be difficult to withdraw through the tight portion of the ureter.

Generally, stones are broken up until the fragments appear to be small enough to ensnare safely. Complete fragmentation may be hindered, however, by vision, ureteral edema, and fear of proximal migration. Even when the stones are adequately broken, stone fragments may be left behind because conventional baskets are not optimized for removal of shattered stones. Stone fragments left in the body may not be excreted as quickly or as completely as desired. Accordingly, there is a need in the art for an improved surgical instrument for fragmenting and/or extracting stones and the like.

SUMMARY OF THE INVENTION

The present invention provides a surgical instrument which solves at least some of the above-noted problems. In accordance with one aspect of the present invention a surgical instrument includes, in combination, an outer sheath having a proximal end and a distal end and an inner core longitudinally extending through the core and longitudinally movable relative to the core. The outer sheath has a basket sized for entrapping the stones and located near the distal end of the outer sheath. The distal end of the inner core is adapted to engage and fragment the stones.

In accordance with another aspect of the present invention, a surgical instrument for fragmenting and extracting stones comprising, in combination, an outer sheath having a proximal end and a distal end and an inner core longitudinally extending through the core and longitudinally movable relative to the core. The outer sheath has a basket sized for entrapping the stones and located near the distal end of the outer sheath. The distal end of the inner core is longitudinally moveable from a retracted position within the basket to an extended position past the distal end of the outer sheath.

In accordance with yet another aspect of the present invention, a surgical instrument for fragmenting and extracting stones comprising, in combination, an outer sheath having a proximal end and a distal end and an inner core longitudinally extending through the core and longitudinally movable relative to the core. The outer sheath has a basket sized for entrapping the stones and located near the distal end of the outer sheath. The distal end of the inner core is longitudinally moveable from a retracted position within the basket to an extended position past the distal end of the outer sheath. The distal end of the inner core is adapted to engage and fragment the stones. Longitudinal movement of the inner core relative to the outer sheath transforms the basket from an expanded condition to a collapsed condition. The basket has a profile small in the collapsed condition than the expanded condition.

From the foregoing disclosure and the following more detailed description of various preferred embodiments it will be apparent to those skilled in the art that the present invention provides a significant advance in the technology and art of surgical instruments. Particularly significant in this regard is the potential the invention affords for providing a high quality, easy to operate, reliable instrument. Additional features and advantages of various preferred embodiments will be better understood in view of the detailed description provided below.

BRIEF DESCRIPTION OF THE DRAWINGS

These and further features of the present invention will be apparent with reference to the following description and drawings, wherein:

FIG. 1 is an elevational view, in cross-section, of a fragmentation and extraction device according to the present invention showing the device in an operating or free condition;

FIG. 2 is an elevational view, in cross-section, of the fragmentation and extraction device of FIG. 1 showing the device in an inserting/extracting or collapsed condition;

FIG. 3 is an elevational view, in cross-section, of the fragmentation and extraction device of FIGS. 1 and 2 showing the device in an operating condition with an inner core retracted in a basket;

Figure 4:
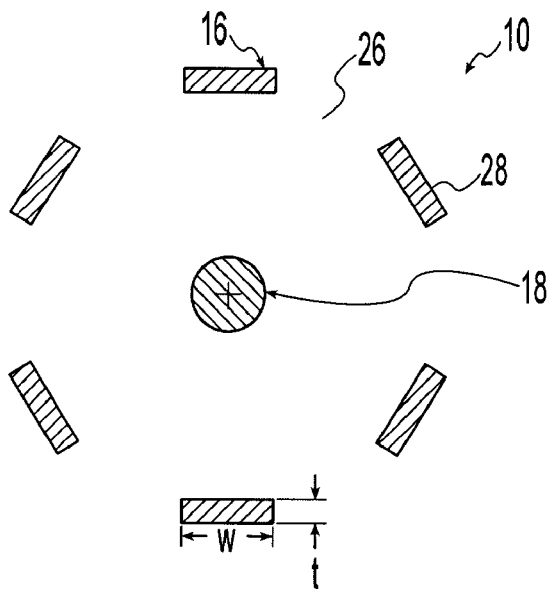
FIG. 4 is an enlarged, cross-sectional view taken along line 4-4 of FIG. 1.
Figure 5:
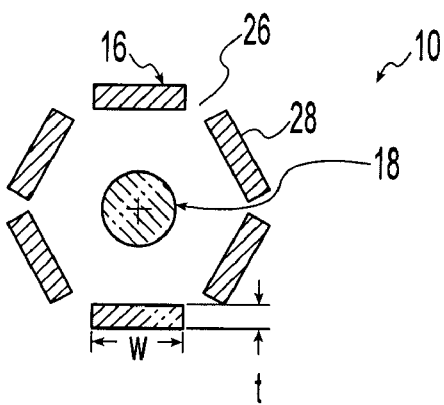
FIG. 5 is an enlarged, cross-sectional view taken along line 5-5 of FIG. 2.
Figure 6:
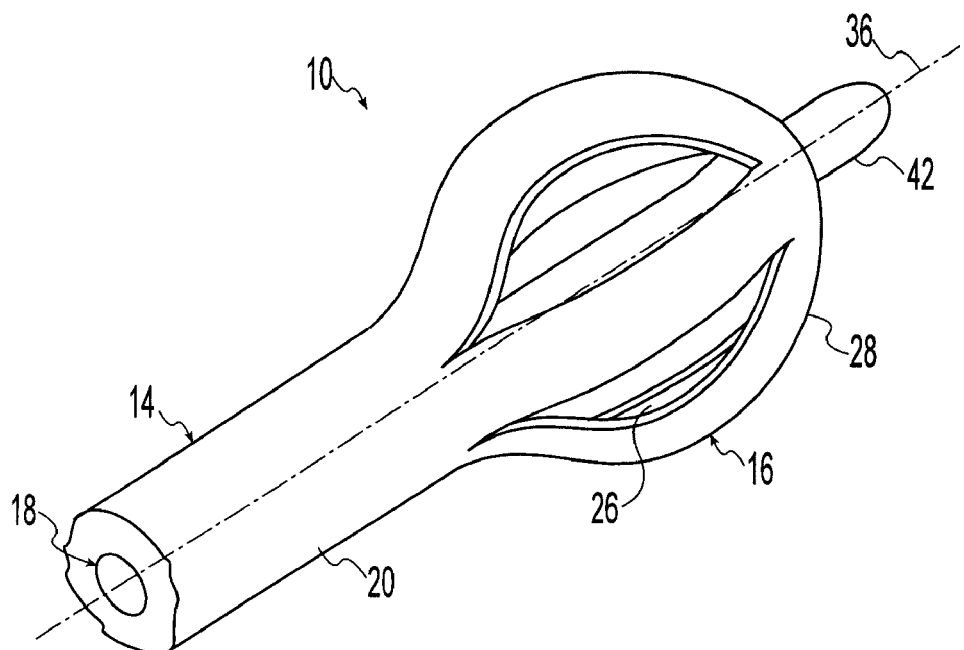
FIG. 6 is an enlarged, fragmented, perspective view, showing a distal end portion of the fragmentation and extraction device of FIGS. 1 to 5.
Figure 7:
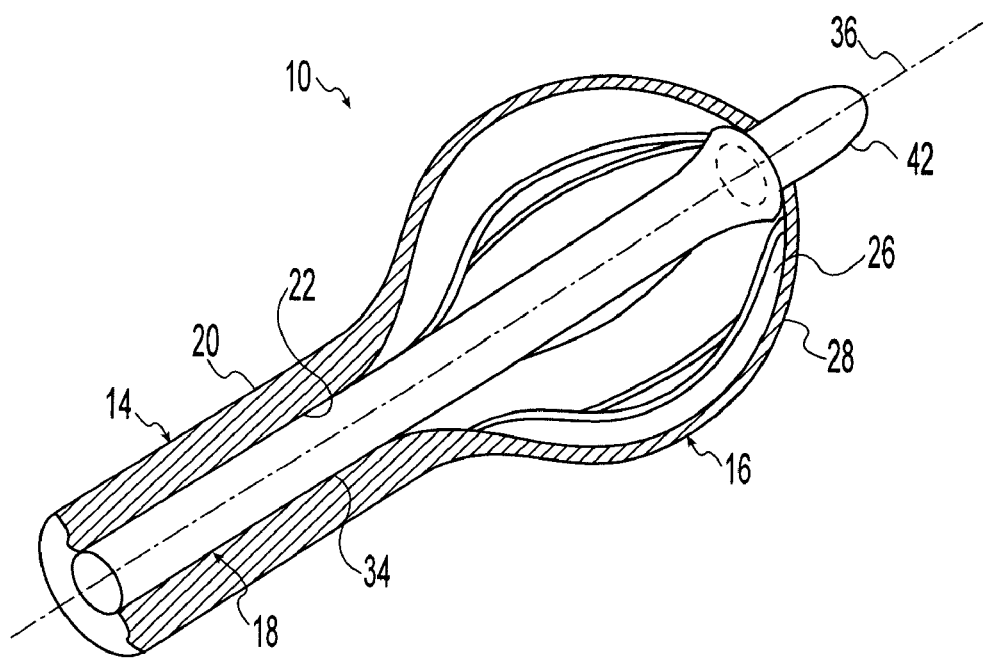
FIG. 7 is an enlarged, fragmented, perspective view, similar to FIG. 6 but partially in cross-section for clarity.

It should be understood that the appended drawings are not necessarily to scale, presenting a somewhat simplified representation of various preferred features illustrative of the basic principles of the invention. The specific design features of a surgical instrument as disclosed herein, including, for example, specific dimensions, orientations, and shapes of the outer sheath and inner core will be determined in part by the particular intended application and use environment. Certain features of the illustrated embodiments have been enlarged or distorted relative to others to facilitate visualization and clear understanding. In particular, thin features may be thickened, for example, for clarity or illustration. All references to direction and position, unless otherwise indicated, refer to the orientation of the surgical device illustrated in the drawings. In general, front or forward refers to a rightward direction within the plane of the paper in FIG. 1 toward the free tip of the inner core and the distal end of the device, and rear or rearward refers to a leftward direction within the plane of the paper in FIG. 1 toward the proximal end of the device and away from the free tip or distal end of the inner core.

DETAILED DESCRIPTION OF CERTAIN PREFERRED EMBODIMENTS

It will be apparent to those skilled in the art, that is, to those who have knowledge or experience in this area of technology, that many uses and design variations are possible for the surgical instrument disclosed herein. The following detailed discussion of various alternative and preferred embodiments will illustrate the general principles of the invention with reference to a surgical instrument or fragmentation and fragmentation basket suitable for fragmenting and/or removing ureteral stones from a human patient's body. Other embodiments suitable for other applications will be apparent to those skilled in the art given the benefit of this disclosure.

As best shown in FIGS. 1 to 7, a fragmentation and extraction device 10 according to the present invention is preferably utilized in conjunction with an endoscope 12 such as a ureteroscope or other suitable instrument. The fragmentation and extraction device 10 includes an outer member or sheath 14 having a collapsible basket 16 and an inner member or core 18 longitudinally extending through the outer sheath 14. The collapsible basket 16 of the outer sheath 14 serves as a retrieval and entrapment basket which can be selectively altered between an operating or free condition wherein the collapsible basket 16 is expanded radially outward to retrieve and entrap stones (best shown in FIGS. 1 and 4) and an inserting/extracting or collapsed condition wherein the basket is collapsed radially inward to a reduced profile to permit insertion and withdrawal of the device 10 and to entrap stones (best shown in FIGS. 2 and 5) as described in more detail hereinafter. The inner core 18 selectively collapses and therefore straightens the collapsible basket 16 and also selectively fragments stones as described in more detail hereinafter.

The elongate outer member or sheath 14 is generally tubular-shaped having a proximal end 14a at the endoscope 12 and a free distal end 14b for insertion into the patient. The outer sheath 14 has a cylindrically shaped outer surface 20 for most of its length and a longitudinally extending inner passage 22.

The outer surface 20 of the outer sheath 14 is preferably sized and shaped for close passage through a working channel of the endoscope 12 and insertion into a lumen or cavity of a human patient. The outer sheath 14 is preferably the radially outermost component of the device 10 such that passage through the working channel of the endoscope 12 directly acts on the outer surface of the outer sheath 14 as described in more detail hereinafter. The inner passage 22 is preferably sized and shaped for close receipt of the inner core 18 as described in more detail hereinafter.

The illustrated collapsible basket 16 is formed near a forward or distal end of the outer sheath 14 and is generally bulb shaped but the collapsible basket 16 can alternatively be of any suitable shape. The collapsible basket 16 defines a hollow interior space 24 radially larger than the inner passage 22 such that there is free or open space in the collapsible basket 16 for entrapping stones within the collapsible basket 16 even while the inner core 18 passes entirely through the collapsible basket 16. The outer sheath 14 is perforated at the collapsible basket 16 by a plurality of openings 26. The openings 26 are preferably sized and shaped for the passage of stones into the interior space 24 of the collapsible basket 16 (best shown in FIGS. 1 and 4). The illustrated openings 26 are slits extending in a longitudinal direction and equally spaced about the circumference of the outer sheath 14. The slits 26 preferably do not entirely extend to the distal end of the outer sheath 14. The openings 26 can alternatively have any suitable size and shape. The spaced apart slits or openings 26 form separate longitudinally extending and circumferentially spaced apart bridging or connecting arms 28. The openings 26 and bridging arms 28 are preferably sized and shaped such that the collapsible basket 16 is resiliently collapsible to a substantially cylindrical shape with the openings 26 closed or substantially closed when the collapsible basket 16 is in the collapsed condition (best shown in FIGS. 2 and 5). The illustrated bridging arms 28 are rectangular-shaped in cross-section wherein the width w is greater than the wall thickness t. It is noted that the wall thickness t of the bridging arms 28 is preferably less than the wall thickness of the remaining portion of the outer sheath 14 but alternatively can be equal or larger. It is also noted that while the illustrated collapsible basket 16 has six openings and six bridging arms 28, there can alternatively be a fewer or greater number of openings 26 and/or bridging arms 28 within the scope of the present invention.

The illustrated inner passage 22 extends entirely through the outer sheath 14 such that there is an opening 30 at the distal end 14b of the outer sheath 14. A rearward facing engagement surface or abutment 32 encircles the opening 30 in the interior of the collapsible basket 16 which cooperates with the inner core 18 to collapse the collapsible basket 16 as described in more detail hereinafter. It is noted that while the illustrated abutment 32 is in the form of an annular-shape or ring about the opening 30, the abutment 32 can alternatively have any suitable size, shape, and location.

The collapsible basket 16 is preferably formed of a suitable resilient material such that the collapsible basket 16 elastically deforms from its preformed or un-stressed operating condition to its inserting/extracting condition when suitable forces are applied by the inner core 18 and resiliently returns to its operating shape when the forces are removed. It is believed that suitable materials include polymers and elastomers. The outer sheath 14 and the collapsible basket 16 are preferably formed of the same material but alternatively can be formed of different materials. The outer sheath 14 and the collapsible basket 16 are preferably formed unitary, that is, as a single body of continuous material formed by, for example, molding, co molding or over molding. It is noted that alternatively the collapsible basket 16 can be secured or attached to the outer sheath 14 in any suitable manner.

The elongate inner core 18 is generally cylindrically-shaped having a proximal end 18a at the endoscope 12 and a free distal end 18b for insertion into the patient. The inner core 18 preferably has a length that can extend all the way through the outer sheath 14 including the collapsible basket 16 and pass through the opening 30 in the distal end 14b of the outer sheath 14. A cylindrical outer surface 34 of the inner core 18 is sized and shaped to be closely and slidingly received in the inner passage 22 of the outer sheath 14 so that the inner core 18 can slide within the inner passage 22 along a central axis 36. The illustrated inner core 18 forms a forward facing engagement surface or abutment 38 near its distal end 18b which is sized and shaped to cooperate with the abutment 32 of the outer sheath 14. The illustrated abutment 38 is in the form of an annular-shape or ring encircling the central axis 36 of the inner core 18 and is formed by an increased diameter portion 40 of the inner core 18. The abutment 38 can alternatively be formed by a reduced diameter portion or in any other suitable manner. It is noted that while the illustrated abutment 38 is annular or ring-shaped about the inner core 18 near its distal end 18b, the abutment 38 can alternatively have any suitable size, shape, and location. The forward or distal end 18b of the illustrated inner core 18 is provided with a nose 42 sized and shaped to pass through the opening 30 and sized and shaped to fragment stones. The illustrated nose 42 is generally dome-shaped but other suitable shapes can be utilized.

The inner core 18 is preferably formed of a suitable semi-rigid or rigid material, such that once the abutments 32, 38 are engaged, forward movement of the inner core 18 relative to the outer sheath 14 elastically deforms the collapsible basket 16 from its preformed or un-stressed operating condition to its inserting/extracting or collapsed condition. Alternatively, the inner core 18 may be a hybrid of a rigid terminal section for fragmentation, and a more flexible proximal length that would allow for easier passage of the device 10 through the ureteroscope 12. Suitable materials are believed to include polymers, elastomers, and metals.

The inner core 18 extends through the inner passage 22 of the outer sheath 14 and can be longitudinally moved relative to the outer sheath 14. The inner core 18 slides freely within the inner passage 22 of the outer sheath 14. The inner core 18 is preferably suitably connected to a movement device or handle 44 of the endoscope 12 so that the surgeon can selectively control and actuate the inner core 18 relative to the outer sheath 14. As best shown in FIG. 1, the inner core 18 can be moved in a forward direction so that the inner core 18 passes entirely through the collapsible basket 16 and extends through the opening 30 at the forward or distal end 14b of the outer sheath 14. In this extended position, the nose 42 of the inner core 18 is located forward of the distal end 14b of the outer sheath 14 so that the nose 42 can initially fragment stones located forward of the device 10 prior to entrapment of the stones in the collapsible basket 16. As best shown in FIG. 2, the inner core 18 can be moved further forward relative to the outer sheath 14 once the abutments 32, 38 are engaged so that the inner core 18 applies a tensile force or load to the outer sheath 14 which elastically deforms the collapsible basket 16 to its collapsed condition. This collapsed condition produces a small profile for passage of the device 10 through the ureteroscope 12 and extraction down the ureter. As best shown in FIG. 3, the inner core 18 can also be moved in a rearward direction relative to the outer sheath 14 so that the nose 42 is in a retracted position within the collapsible basket 16. In this retracted position, the nose 42 of the inner core 18 is located within the collapsible basket 16 so that the nose 42 can initially or additionally fragment stones entrapped within the collapsible basket 16.

Figure 8:
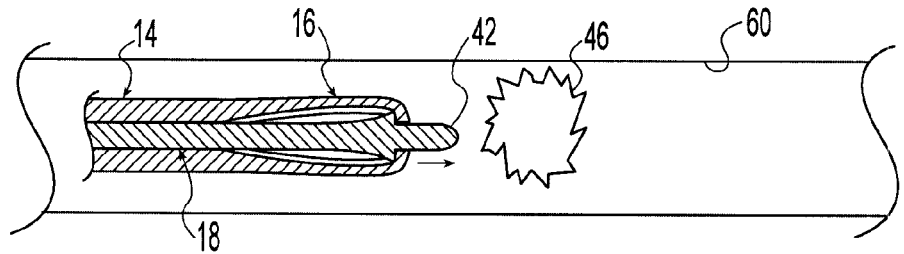
FIG. 8 is a diagrammatic view of the device of FIGS. 1 to 7 showing the fragmentation and extraction device approaching a stone in a lumen of a body tract.

As best shown in FIG. 8, the device 10 is initially passed through the working channel of the ureteroscope 12 to a stone 46 located within a lumen or other cavity 60 of a patent so that fragmentation, capture, and/or extraction of the stone 46 may be accomplished under direct vision. Vision is accomplished by a fiber optic device or other suitable vision unit incorporated into the device 10. then endoscope 12, or separate of both the device 10 and the endoscope 12. During initial insertion, the collapsible basket 16 is preferably in its insertion/extraction or collapsed condition.

Figure 9:
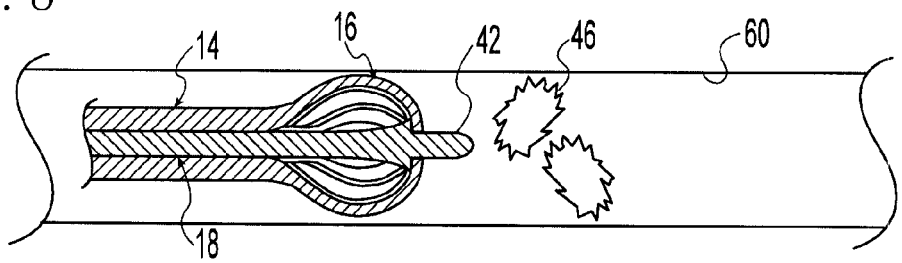
FIG. 9 is a diagrammatic view of the device of FIGS. 1 to 7 showing the fragmentation and extraction device fragmenting a stone in a lumen of a body tract.

As best shown in FIG. 9, the stone 46 can be initially fragmented with the exposed tip or nose 42 of the inner core 18 if desired, as the nose 42 protrudes slightly through the opening 30 at the distal end 14b of the outer sheath 14. Initial fragmentation may be desired when the stone 46 is too large to easily engage and capture with the collapsible basket 16. Energy is delivered by the inner core 18 to fragment the stone 46. Energy can be by mechanical energy delivered by direct impact with the stone 46 or delivered by an energy source 48 (FIGS. 13 to 15) of the device which transmits energy to the stone 46 through the inner core 18. Preferably, the stone 46 is initially fragmented only as needed to permit capture by the collapsible basket 16 to minimize small fragments produced outside the collapsible basket 16. It is noted that in some cases it may be desirable to engage and capture the stone 46 without initial fragmentation, such as when the stone 46 is small enough to be easily engaged and captured by the collapsible basket 16.

Figure 10:
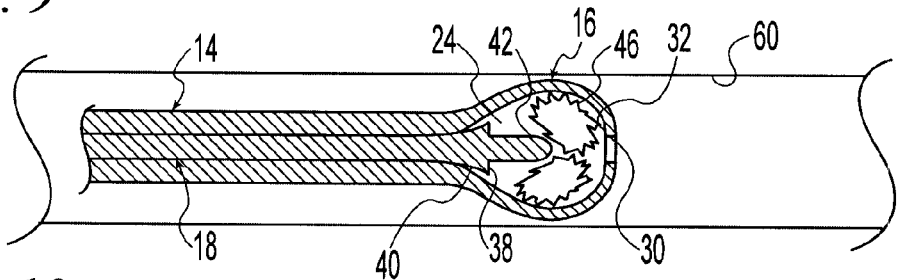
FIG. 10 is a diagrammatic view of the device of FIGS. 1 to 7 showing the fragmentation and extraction device capturing stones in a lumen of a body tract.
Figure 11:
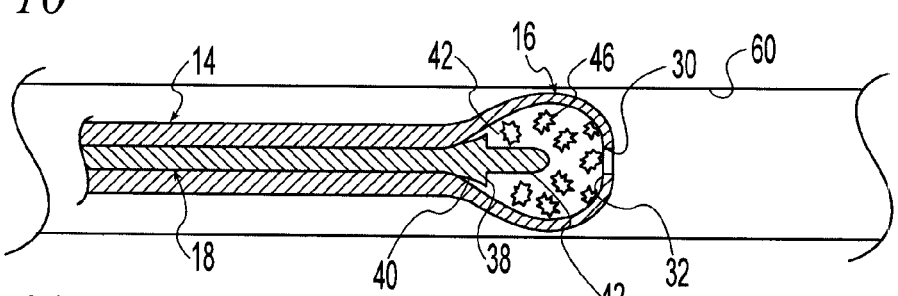
FIG. 11 is a diagrammatic view of the device of FIGS. 1 to 7 showing the fragmentation and extraction device fragmenting stones within a basket located in a lumen of a body tract.

As best shown in FIG. 10, once the stones 46 are of adequate size for capture, the inner core 18 is pulled back by the surgeon actuating the handle 44 so that the collapsible basket 16 resiliently returns to its expanded or operating condition. The stones 46 are then engaged and passed into the inner space or lumen 24 of the collapsible basket 16 by the surgeon manipulating the entire device 10. With the stones 46 located within the collapsible basket 16, the surgeon can additionally or initially fragment the entrapped stones 46 within the collapsible basket 16 if desired. It is noted that in some cases it may be desirable to engage and capture the stone 46 without additional or initial fragmentation, such as when the stone 46 is small enough to be extracted without fragmentation. As best shown in FIG. 11, the inner core 18 can be retracted and re-extended within the collapsible basket 16 to directly contact the stones 46 which are located within the collapsible basket 16 to provide for fragmentation of the stones 46 through conducted energy or through the direct application of mechanical energy. It is noted that the collapsible basket 16 can be partially or fully collapsed to additionally secure the stones 46 during this fragmentation if desired.

Figure 12:
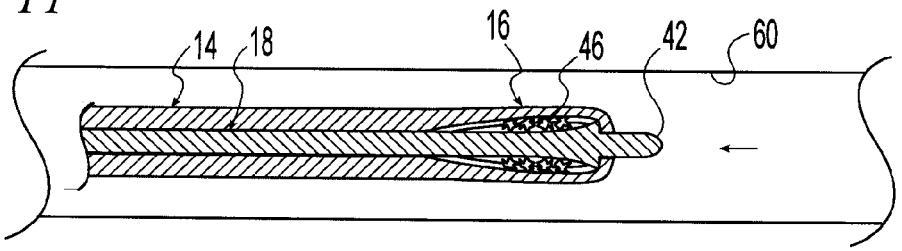
FIG. 12 is a diagrammatic view of the device of FIGS. 1 to 7 showing the fragmentation and extraction device extracting stones from a lumen of a body tract.

With the stones 46 in the collapsible basket 16 the surgeon has several options for extracting the stones 46 and the device 10. First, the surgeon can remove the entire device 10 as is with the stones 46, while the collapsible basket 16 remains in its expanded condition, by sliding the device 10 down the ureter into the patient's bladder. Second, the surgeon can advance the inner core 18 to collapse the collapsible basket 16 to its insertion/extraction condition. As best shown in FIG. 12, the fully reduced profile of the device 10 in the insertion/extraction allows for easy removal of the entire device 10 with the stones 46 entrapped therein. Third, if a stone or stones are preventing complete collapse of the collapsible basket 16, the surgeon can reduce the profile of the collapsible basket 16 and further secure stone entrapment by withdrawing the entire device 10 partially back within the working channel of the ureteroscope 12. By withdrawing the outer sheath 14 into the working channel of the ureteroscope 12, the collapsible basket 16 is further narrowed and fully collapsed much like a conventional basket being withdrawn into its outer sheath. As such, the inner core 18 better impacts the firmly held stones 46 which are preventing complete withdrawal of the collapsible basket 16. It is noted that, if necessary, additional stone fragmentation may be performed when the collapsible basket 16 is collapsed or partially collapsed and the stones 46 are more firmly ensnared prior to or during any of these steps for extracting the stones 46.

Under some conditions, some stone fragments broken up by the inner core 18 within the collapsible basket 16 may spontaneously escape through the openings 26 of the collapsible basket 16. These pieces or fragments may be reengaged and the cycle of engagement and fragmentation continued until all particles are entrapped and extracted or deemed passable without extraction.

Figure 13:
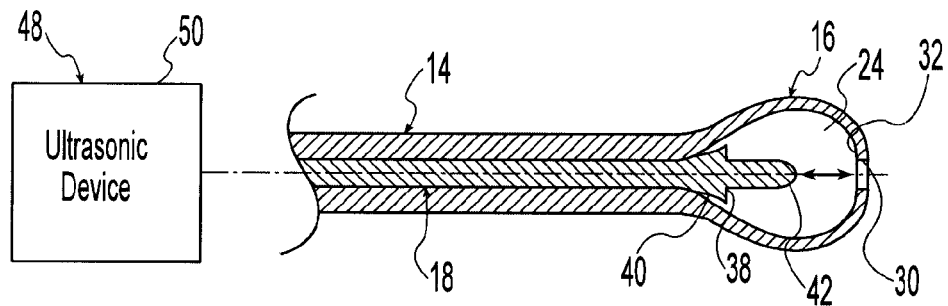
FIG. 13 is a diagrammatic view of second embodiment of the device according to the present invention, showing the core coupled to an ultrasonic device.
Figure 14:
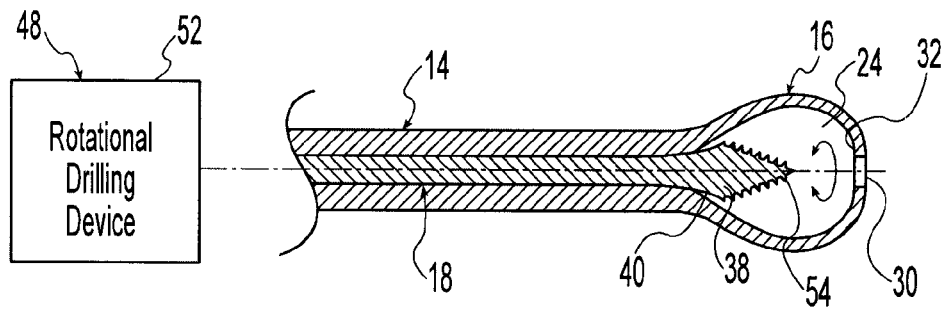
FIG. 14 is a diagrammatic view of second embodiment of the device according to the present invention, showing the core coupled to a rotational drilling device.
Figure 15:
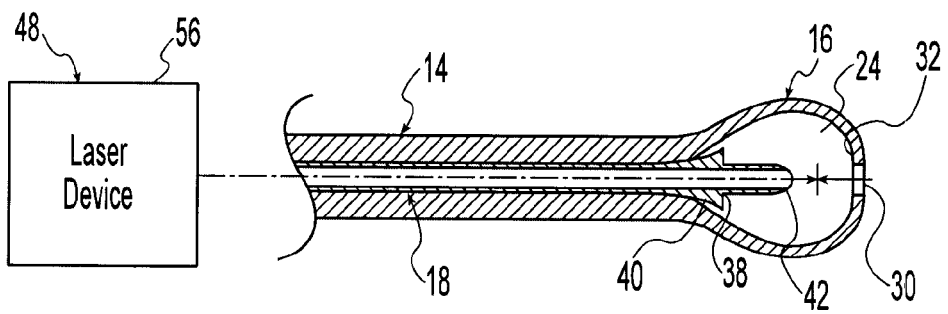
FIG. 15 is a diagrammatic view of second embodiment of the device according to the present invention, showing the core coupled to a laser device.
Figure 16:
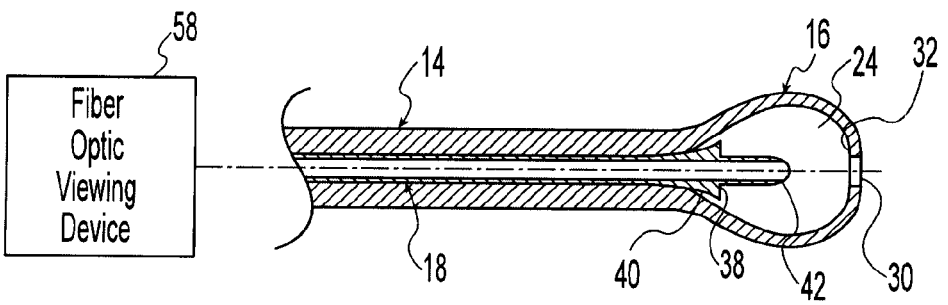
FIG. 16 is a diagrammatic view of second embodiment of the device according to the present invention, showing the core coupled to a fiber optic viewing device.

As noted hereinabove, fragmentation energy other than mechanical impact can be supplied to the stones through the inner core 18. An energy source 48 of any suitable type can be coupled or connected to the inner core 18. As best shown in FIG. 13, the energy source 48 can be pneumatic, ultrasonic or other vibrating device 50 useful for stone fragmentation. As best shown in FIG. 14, the energy source 48 can be in the form of a rotational drilling device 52 which rotates a drill head or bit 54 located at the distal end 14b of the inner core 18 useful for stone fragmentation. The drilling device 52 can alternatively rotate the drill bit 54 alone or the entire inner core 18. Alternatively, a hollow passage of the inner core 18 can allow the transmission of hydraulic or pneumatic energy to propel the drill bit 54 or other mobile fragmentation tip. As best shown in FIG. 15, the energy source 48 can be in the form of a laser device 56 suitable for stone fragmentation. It is noted that in each of these embodiments, at least a portion of the inner core 18 comprises a material suitable to transmit or conduct the ballistic, ultrasonic, rotational, laser, or other desired form of energy. As best shown in FIG. 16, the inner core 18 can also alternatively be coupled to a fiber optic viewing device 58 which extends the length of the inner core 18 for viewing at the distal end 18b of the inner core 18. It is noted that each of these alternatives can be used alone or in combination either simultaneously or consecutively. For example, the inner core 18 with a blunt nose 42 can be used to engage the stone, once the stone is engaged this inner core 18 is removed from the outer sheath 14 and an inner core 18 with the rotational drill bit 54 is placed within the outer sheath 14 to fragment the stone into particles. Such a inner core 18 used for rotational purposes but not for collapsing the collapsible basket 16 can be quite flexible throughout most of its length. It is further noted that the inner core 18 may effect mechanical fragmentation of the stones through direct exertion of pressure on the stones. For example, once the stones are trapped within the collapsible basket 16, an inner core 18 in the form of a rigid solid member may forcibly fragment the stones through direct mechanical pressure and without the delivery of conducted energy.

It is apparent from the above detailed disclosure that fragmentation and extraction device 10 according to the present invention provides many unique benefits over existing baskets. For example, the collapsible basket 16 is formed by the terminus of the outer sheath 14 and is collapsed upon movement of the inner core 18 to allow for stone engagement and retrieval. The inner core 18 uniquely provides the method of closing or changing the configuration of the collapsible basket 16. Additionally, the device allows for initial stone fragmentation via the exposed nose 42 of the inner core 18 prior to entrapment of the stone in the collapsible basket 16. Furthermore, the device 10 allows for additional or initial fragmentation of the entrapped stone within the collapsible basket 16 without the passage or use of additional devices. Moreover, the device 10 allows for disruption of the entrapped stone by direct application of mechanical force by the surgeon transmitted through the inner core 18. Even moreover, the collapsible basket 16 is constructed in a manner which entraps smaller fragments than prior art wire baskets.

It is also apparent that the fragmentation and extraction device 10 according to the present invention is a combination fragmentation and retrieval device that with a single device allows for optional initial stone fragmentation outside the collapsible basket 16, stone entrapment or capture, additional or initial stone fragmentation within the collapsible basket 16 if desired, and stone removal or extraction if desired. The fragmentation and extraction device 10 thus eliminates the need for separate fragmentation and extraction devices, decreases the necessity of device exchanges, and allows for continued and more efficient fragmentation once the stone is ensnared within the collapsible basket 16. Fragmentation of ensnared stones should allow for more efficient fragmentation and reduce proximal migration of large particles.

From the foregoing disclosure and detailed description of certain preferred embodiments, it will be apparent that various modifications, additions and other alternative embodiments are possible without departing from the true scope and spirit of the present invention. The embodiments discussed were chosen and described to provide the best illustration of the principles of the present invention and its practical application to thereby enable one of ordinary skill in the art to utilize the invention in various embodiments and with various modifications as are suited to the particular use contemplated. All such modifications and variations are within the scope of the present invention as determined by the appended claims when interpreted in accordance with the benefit to which they are fairly, legally, and equitably entitled

What is claimed is:

1. A surgical instrument for use with an endoscope having a working channel to fragment and extract stones from a patient, said surgical instrument comprising, in combination:
    an outer sheath having a proximal end, a distal end, and a basket therebetween;
    wherein the basket is sized for entrapping the stones and located near the distal end of the outer sheath;
    wherein the outer sheath and the basket are formed unitarily as a single body of continuous material;
    wherein the basket transforms between an expanded condition forming a hollow interior space for capturing the stones and a collapsed condition having a profile sized smaller than the expanded condition for insertion of the basket into the patient and withdrawal of the basket from the patient;
    wherein a periphery of the basket has a plurality of spaced apart openings sized and shaped for passage of the stones into the interior space when in the expanded condition;
    an inner core longitudinally extending through the outer sheath and into the hollow interior and longitudinally movable relative to the outer sheath;
    wherein the inner core has a proximal end and a free distal end, wherein the free distal end is unsecured to the outer sheath;
    wherein longitudinal movement of the inner core relative to the outer sheath transforms the basket from the expanded condition to the collapsed condition;
    wherein the distal end of the outer sheath is provided with an opening so that the free distal end of the inner core can move through the opening and past the distal end of the outer sheath
    wherein the outer sheath has an outer surface sized and shaped for close passage through the working channel and into a lumen or cavity of the patient; and
    wherein the outer sheath is the radially outermost component of the instrument such that passage through the working channel directly acts on the outer surface of the sheath.

2. The surgical instrument according to claim 1, wherein the basket is preformed in the expanded condition and resiliently returns to the expanded condition from the collapsed condition upon removal of force applied by the inner core.

3. The surgical instrument according to claim 1, wherein an abutment of the inner core engages an abutment of the outer sheath to resiliently deform the basket from the expanded condition to the collapsed condition upon longitudinal movement of the inner core relative to the outer sheath in a direction away from the proximal end of the outer sheath and toward the distal end of the outer sheath.

4. The surgical instrument according to claim 3, wherein the abutment of the outer sheath encircles an opening in the distal end of the outer sheath so that free distal end of the inner core moves through the opening and is located past the distal end of the outer sheath when the abutment of the inner core engages the abutment of the outer sheath.

5. The surgical instrument according to claim 1, wherein the distal end of the outer sheath is provided with an opening so that the free distal end of the inner core can move through the opening and past the distal end of the outer sheath.

6. The surgical instrument according to claim 1, wherein the distal end of the inner core extends past the distal end of the sheath when the basket is in the collapsed condition.

7. The surgical instrument according to claim 1, wherein the free distal end of the inner core is adapted to engage and fragment the stones when the stones are located within the hollow interior of the space of the basket and when the stones are located outside the hollow interior space of the basket.

8. A surgical instrument for use with an endoscope having a working channel to fragment and extract stones from a patient, said surgical instrument comprising, in combination:
    an outer sheath having a proximal end, a distal end, and a basket therebetween;
    wherein the basket is sized for entrapping the stones and located near the distal end of the outer sheath;
    wherein the outer sheath and the basket are formed unitarily as a single body of continuous material;
    wherein the basket transforms between an expanded condition forming a hollow interior space for capturing the stones and a collapsed condition having a profile sized smaller than the expanded condition for insertion of the basket into the patient and withdrawal of the basket from the patient;
    wherein a periphery of the basket has a plurality of spaced apart openings sized and shaped for passage of the stones into the interior space when in the expanded condition;
    an inner core longitudinally extending through the outer sheath and longitudinally movable relative to the outer sheath;
    wherein the inner core has a proximal end and a free distal end, wherein the free distal end is unsecured to the outer sheath;

wherein the free distal end of the inner core extends past the distal end of the sheath when the basket is in the collapsed condition;

wherein longitudinal movement of the inner core relative to the outer sheath away from the proximal end of the outer sheath and toward the distal end of the outer sheath engages the inner core with the outer sheath to apply a tensile force to the outer sheath which lengthens the outer sheath by collapsing the basket from the expanded condition to the collapsed condition;

wherein the outer sheath has an outer surface sized and shaped for close passage through the working channel and into a lumen or cavity of the patient; and wherein the outer sheath is the radially outermost component of the instrument such that passage through the working channel directly acts on the outer surface of the sheath.

9. The surgical instrument according to claim 8, wherein the basket is preformed in the expanded condition and resiliently returns to the expanded condition from the collapsed condition upon removal of force applied by the inner core.

10. The surgical instrument according to claim 8, wherein an abutment of the inner core engages an abutment of the outer sheath to resiliently deform the basket from the expanded condition to the collapsed condition upon longitudinal movement of the inner core relative to the outer sheath in a direction away from the proximal end of the outer sheath and toward the distal end of the outer sheath.

11. The surgical instrument according to claim 10, wherein the abutment of the outer sheath encircles an opening in the distal end of the outer sheath so that the free distal end of the inner core moves through the opening and is located past the distal end of the outer sheath when the abutment of the inner core engages the abutment of the outer sheath.

12. The surgical instrument according to claim 8, wherein the distal end of the outer sheath is provided with an opening so that the free distal end of the inner core can move through the opening and past the distal end of the outer sheath.

13. The surgical instrument according to claim 8, wherein the free distal end of the inner core is adapted to engage and fragment the stones when the stones are located within the hollow interior of the space of the basket and when the stones are located outside the hollow interior space of the basket.

14. A surgical instrument for use with an endoscope having a working channel to fragment and extract fragmenting and extracting stones from a patient comprising, in combination:

an outer sheath having a proximal end, a distal end, and a basket therebetween;

wherein the basket is sized for entrapping the stones and located near the distal end of the outer sheath;

wherein the basket transforms between an expanded condition forming a hollow interior space for capturing the stones and a collapsed condition having a profile sized smaller than the expanded condition for insertion of the basket into the patient and withdrawal of the basket from the patient;

wherein a periphery of the basket has a plurality of spaced apart openings sized and shaped for passage of the stones into the interior space when in the expanded condition;

an inner core longitudinally extending through the outer sheath and longitudinally movable relative to the outer sheath;

wherein the inner core has a proximal end and a free distal end, wherein the free distal end is unsecured to the outer sheath;

wherein the distal end of the inner core extends past the distal end of the outer sheath when the basket is in the collapsed condition;

wherein longitudinal movement of the inner core relative to the outer sheath transforms the basket from the expanded condition to the collapsed condition;

wherein the outer sheath has an outer surface sized and shaped for close passage through the working channel and into a lumen or cavity of the patient;

wherein the outer sheath is the radially outermost component of the instrument such that passage through the working channel directly acts on the outer surface of the sheath; and wherein the distal end of the inner core is longitudinally moveable from a retracted position within the basket to an extended position past the distal end of the outer sheath to fragment stones outside the basket.

15. The surgical instrument according to claim 14, wherein an abutment of the inner core engages an abutment of the outer sheath to resiliently deform the basket from the expanded condition to the collapsed condition upon longitudinal movement of the inner core relative to the outer sheath in a direction away from the proximal end of the outer sheath and toward the distal end of the outer sheath.

16. The surgical instrument according to claim 15, wherein the abutment of the outer sheath encircles an opening in the distal end of the outer sheath so that the free distal end of the inner core moves through the opening and is located past the distal end of the outer sheath when the abutment of the inner core engages the abutment of the outer sheath.

17. The surgical instrument according to claim 14, wherein the free distal end of the inner core is adapted to engage and fragment the stones when the stones are located within the hollow interior of the space of the basket and when the stones are located outside the hollow interior space of the basket.

* * * * *